United States Patent
Sankhe et al.

(10) Patent No.: US 9,965,588 B2
(45) Date of Patent: May 8, 2018

(54) FILM TO DICOM CONVERSION

(71) Applicants: Pritesh Sankhe, Bangalore (IN); Mithun Das Gupta, Bangalore (IN)

(72) Inventors: Pritesh Sankhe, Bangalore (IN); Mithun Das Gupta, Bangalore (IN)

(73) Assignee: RICOH CO., LTD., Tokyo (JP)

( * ) Notice: Subject to any disclaimer, the term of this patent is extended or adjusted under 35 U.S.C. 154(b) by 81 days.

(21) Appl. No.: 14/199,086

(22) Filed: Mar. 6, 2014

(65) Prior Publication Data

US 2015/0254401 A1    Sep. 10, 2015

(51) Int. Cl.
G06K 9/00 (2006.01)
G06F 19/00 (2018.01)
H04N 1/00 (2006.01)

(52) U.S. Cl.
CPC ....... G06F 19/321 (2013.01); H04N 1/00127 (2013.01)

(58) Field of Classification Search
USPC .................. 382/128–134, 181–231
See application file for complete search history.

(56) References Cited

U.S. PATENT DOCUMENTS

| | | | | |
|---|---|---|---|---|
| 5,065,437 A * | 11/1991 | Bloomberg | ........ | H04N 1/40062 358/462 |
| 5,162,994 A * | 11/1992 | Torres | ........ | G06K 9/4633 324/339 |
| 5,181,255 A * | 1/1993 | Bloomberg | ........ | G06K 9/6835 382/176 |
| 5,220,403 A * | 6/1993 | Batchelder | ........ | G01N 21/9505 250/358.1 |
| 5,447,153 A * | 9/1995 | Weil | ........ | G06T 5/009 600/300 |
| 5,769,789 A * | 6/1998 | Wang | ........ | G01R 33/28 382/131 |
| 5,815,591 A * | 9/1998 | Roehrig | ........ | G06K 9/3233 378/37 |
| 5,892,840 A * | 4/1999 | Jang | ........ | G06T 7/0012 378/162 |
| 6,035,056 A * | 3/2000 | Karssemeijer | ........ | G06K 9/4633 378/37 |
| 6,263,092 B1 * | 7/2001 | Roehrig | ........ | G06K 9/00 378/37 |
| 6,411,733 B1 * | 6/2002 | Saund | ........ | G06K 9/00456 382/190 |
| 6,858,007 B1 * | 2/2005 | Akselrod | ........ | A61B 6/466 128/916 |

(Continued)

FOREIGN PATENT DOCUMENTS

EP       2403233 A1    1/2012

OTHER PUBLICATIONS

Bishop, T.E. et al., "Light Field Super Resolution," IEEE ICCP, 2009, 10 pages.

(Continued)

*Primary Examiner* — Alex Liew
(74) *Attorney, Agent, or Firm* — Fenwick & West LLP

(57) ABSTRACT

Embodiments digitize radiology films into DICOM format. Radiology films typically include an array of captured images laid out in a grid pattern. To comply with DICOM format, the scanned image of a radiology film is segmented into sub-images and text is extracted from the sub-images to generate DICOM metadata. The sub-images and extracted text metadata are then combined to generate a DICOM-compliant multi-image file.

20 Claims, 14 Drawing Sheets

(56) References Cited

U.S. PATENT DOCUMENTS

| | | | | |
|---|---|---|---|---|
| 2002/0176120 | A1* | 11/2002 | O'Callaghan | H04N 1/38 358/453 |
| 2005/0063579 | A1* | 3/2005 | Lee | G06K 9/34 382/131 |
| 2007/0248254 | A1* | 10/2007 | Mysore Siddu | G06K 9/4638 382/131 |
| 2011/0143811 | A1* | 6/2011 | Rodriguez | G06K 9/00986 455/556.1 |
| 2011/0150323 | A1 | 6/2011 | Hancock et al. | |
| 2017/0193292 | A1* | 7/2017 | Bellert | G06K 9/00456 |

OTHER PUBLICATIONS

Chen, D. et al., "Text Identification in Complex Backgrounds Using SVM," Proceeding of the 2001 IEEE Computer Society Conference on Computer Vision and Pattern Recognition, 2001, 6 pages.

Cho et al., "Modeling the Calibration Pipeline of the Lytro Camera for High Quality Light-Field Image Reconstruction," 2013 IEEE International Conference on Computer Vision, Korea Advanced Institute of Science and Technology, IEEE, 2013, pp. 3280-3287.

Georgiev, T. et al., "Superresolution with Plenoptic Camera 2.0," Adobe Technical Report, Apr. 2009, 9 pages.

Li, C.H. et al., "Minimum Cross Entropy Thresholding," Pattern Recognition, 1993, pp. 617-625, vol. 26, No. 4.

Ng, M.K. et al., "Mathematical Analysis of Superresolution Methodology," IEEE Signal Processing Magazine, May 2003, pp. 62-74, vol. 20 No. 3.

Pérez Nava F. et al., "Simultaneous Estimation of Superresolved Depth and All-In-Focus Images from a Plenopticcamera," 3DTV-CON 2009, IEEE, 2009, 4 pages.

United States Office Action, U.S. Appl. No. 15/785,404, dated Dec. 15, 2017, 14 pages.

\* cited by examiner

FILM TO DICOM CONVERSION

BACKGROUND

Field of Disclosure

This disclosure relates generally to the conversion of radiological film to DICOM-compliant image files.

Description of the Related Art

Physical radiology films document medical images that are captured during medical scans conducted on patients. These images are subsequently used by doctors, researchers, and others to diagnose conditions and develop treatments. Although consulting the physical radiology films is still common in some parts of the world such as India, the size and formatting of these physical radiology films lead to difficulties in transferring them to others and archiving them for storage.

In part to respond to the increased use of computers in clinical applications, the American College of Radiology and the National Electrical Manufacturers Association developed a standard method for transferring images and associated information between devices manufactured by various vendors. These entities developed the Digital Imaging and Communications in Medicine (DICOM) standard. DICOM-compliant files can be transferred between computing systems in a multi-vendor environment.

SUMMARY

Embodiments of the invention digitize radiology films into DICOM format. Radiology films typically include an array of captured images laid out in a grid pattern. To comply with DICOM format, the scanned image of a radiology film is segmented into sub-images and text is extracted from the sub-images to generate DICOM metadata. The sub-images and extracted text metadata are then combined to generate a DICOM-compliant multi-image file.

Embodiments of the invention include methods of processing radiology film images into individual sub-images and metadata that are then combined to generate a DICOM compliant multi-image file. Embodiments of the computer-readable storage medium store computer-executable instructions for performing the steps described above. Embodiments of the system further comprise a processor for executing the computer-executable instructions.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

Figure 1:
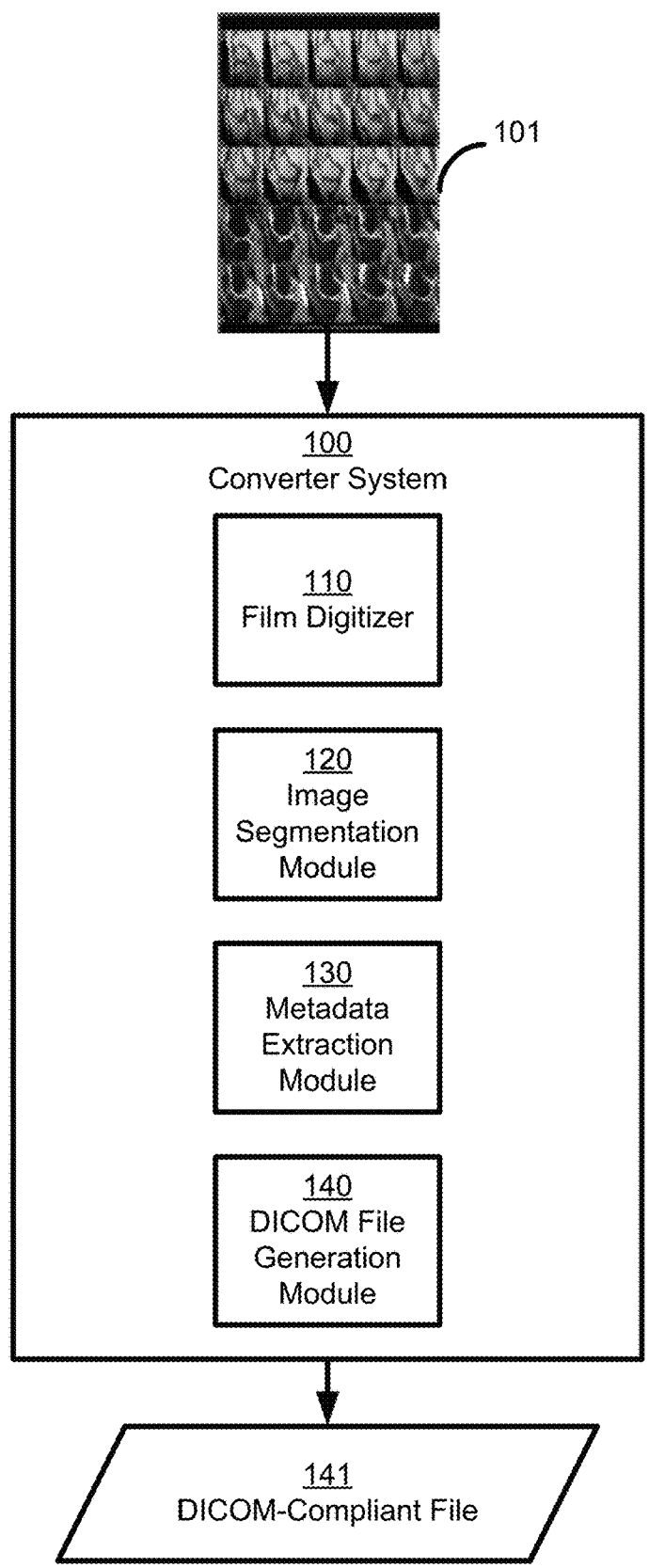
FIG. 1 is a high-level block diagram illustrating an embodiment of an environment for digitizing radiology film into DICOM format.

The Figures (FIGS.) and the following description describe certain embodiments by way of illustration only. One skilled in the art will readily recognize from the following description that alternative embodiments of the structures and methods illustrated herein may be employed without departing from the principles described herein.

DETAILED DESCRIPTION

Embodiments of the invention digitize radiology films into DICOM format. Radiology films typically include an array of captured images laid out in a grid pattern. To comply with DICOM format, the scanned image of a radiology film is segmented into sub-images and text is extracted from the sub-images to generate DICOM metadata. The sub-images and extracted text metadata are then combined to generate a DICOM-compliant multi-image file.

In one embodiment, the radiology film is scanned using a conventional film digitizer. The scan of the radiology film results in one image composed of several sub-images in a grid pattern. By accurately identifying the gridlines between the sub-images, the system can segment the image into sub-image. The gridlines are identified by using an edge-detection pre-processing step followed by a Hough Transform to detect straight lines in the image. Then, by using a statistical analysis that separately considers the length of the detected lines at vertical positions and at horizontal positions, false positives can be removed from the group of detected straight lines. The remaining straight lines are clustered together if they are within a short distance of each other. The mean position of each cluster of lines in the vertical direction is then identified as the center of a vertical gridline, and the mean position of each cluster of lines in the horizontal direction is then identified as the center of a horizontal gridline. The identified vertical and horizontal gridlines are then used to segment the image into sub-images.

In one embodiment, each segmented sub-image is analyzed to detect text regions. The horizontal and vertical edges present in text regions are found by using a Sobel operator along the X direction and using a Sobel operator along the Y direction. Then, dilation along the X direction and dilation along the Y direction are performed to further process the sub-images. The resulting two versions of the sub-image are then combined using a binary AND operation. Additionally, connected component analysis is performed to identify the boundaries of the regions of the sub-image where text is present.

Once regions where text is present are identified, the text regions are processed to enhance the readability of the text before it is read by an Optical Character Recognition (OCR) engine. Each image region identified as containing text is sharpened, a power law transformation is performed, and then Minimum Cross Entropy (to select the best threshold to avoid unnecessary losses of text information during the processing) and hole filing techniques are used on the regions before bit manipulations such as an XOR operation is performed. The resulting processed text region is then prepared for an OCR engine to extract text from the region.

In one embodiment, the result of the text extraction can be evaluated using the Levenshtein Distance between the ground truth (the actual text) and the OCR text. For example, the analysis can be performed using 1-e/c, where e is the Levenshtein distance, and c is the number of characters. The extracted text from the OCR engine can be formatted into DICOM metadata to accompany the sub-image from which it was extracted.

Thus, embodiments of the invention include methods of processing radiology film images into individual sub-images and metadata that are then combined to generate a DICOM compliant multi-image file. Embodiments of the computer-readable storage medium store computer-executable instructions for performing the steps described above. Embodiments of the system further comprise a processor for executing the computer-executable instructions.

System Overview

FIG. 1 is a high-level block diagram illustrating an embodiment of an environment for digitizing radiology film into DICOM format. The environment includes a radiology film 101, a converter system 100, and a DICOM-compliant file 141.

The radiology film 101 is a physical copy of the images obtained, for example, during a medical scan. The images typically contain large intensity variations due to the presence of bone, soft tissue, and other anatomical structures in the images. The film 101 is typically laid out in a grid pattern comprising sub-images and embedded text that identifies the patient, the date, the measurement scale, and other information that may be used as DICOM metadata. The boundaries between the sub-images in the grid pattern are referred to herein as gridlines. The grid and the gridlines may be rotationally skewed with respect to the straight edges of the film 101.

The converter system 100 converts an input radiology film 101 into a DICOM-compliant file 141. The converter system scans the radiology film 101, segments the resulting image into individual sub-images, extracts DICOM metadata from the scanned image, and combines the sub-images with the extracted metadata to generate a DICOM-compliant file 141. The converter system 100 includes a film digitizer 110, an image segmentation module 120, a metadata extraction module 130, and a DICOM file generation module 140.

The film digitizer 110 scans the input radiology film 101 to create a digital image. Any conventional film scanner may be used as film digitizer 110, such as a scanner with resolution of 300 dpi.

The image segmentation module 120 segments the digital image created by the film digitizer 110 into individual sub-images. The image segmentation module 120 identifies straight lines in the image that form the gridlines between sub-images. The operation of the image segmentation module is described in detail below with reference to FIGS. 3-8.

The metadata extraction module 130 extracts DICOM metadata from the individual sub-images identified by the image segmentation module 120. The metadata extraction module 130 detects text regions within the sub-image, processes the text regions to enhance the clarity of the text, and performs text recognition on the text of the regions. The operation of the metadata extraction module 130 is described in detail below with reference to FIGS. 9-13.

The DICOM file generation module 140 combines the individual sub-images with their respective metadata, including text from text regions within the sub-images to generate a DICOM-compliant file 141. The DICOM-compliant file 141 is typically a multi-image file with metadata that provides patient information and information about the image in a standardized format, for example National Electrical Manufacturers Association (NEMA) standard PS3, 2011 version. The operation of the DICOM file generation module 140 is described in detail below with reference to FIG. 14.

Figure 2:
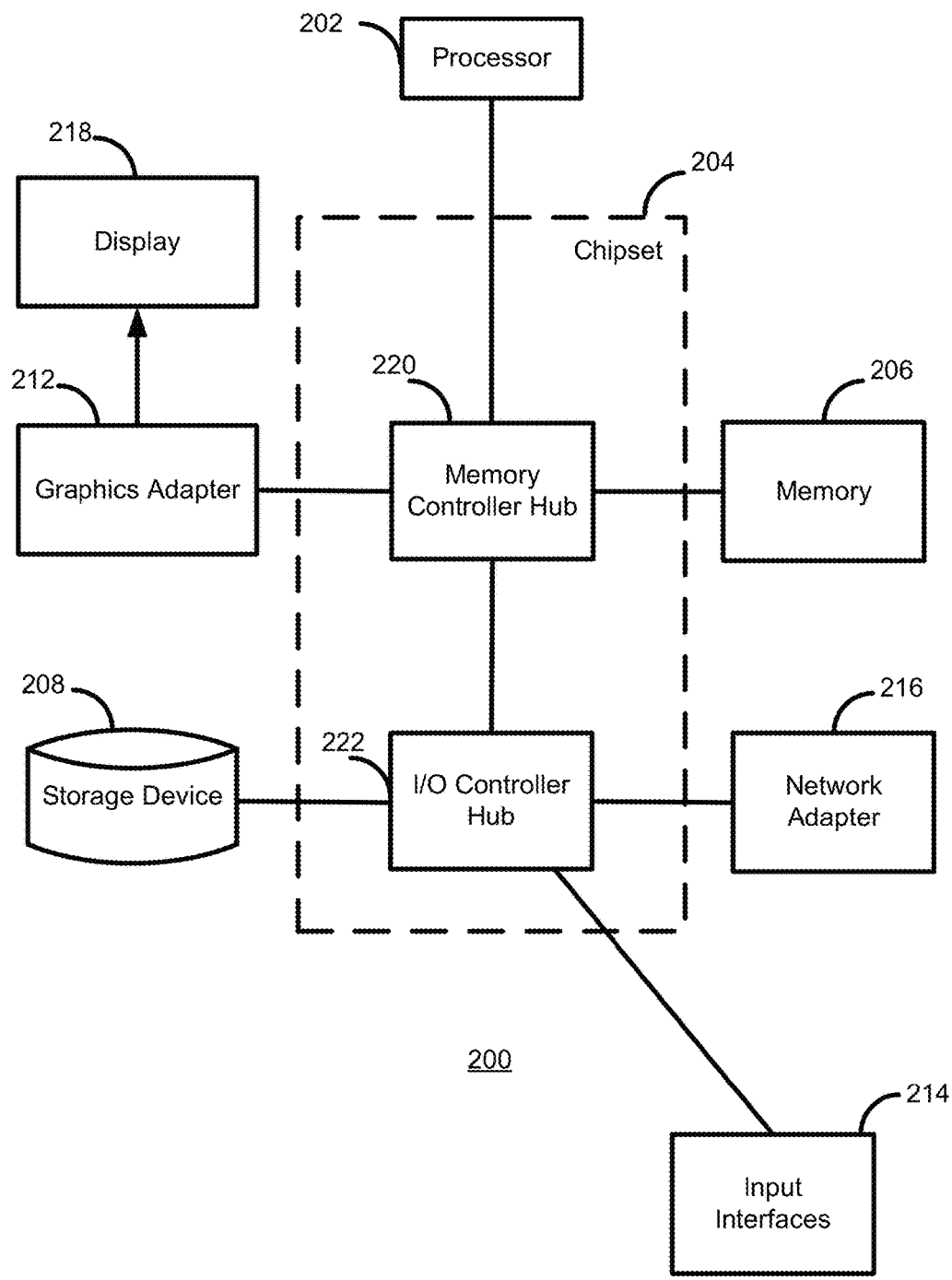
FIG. 2 is a block diagram illustrating an example computer for implementing the converter system shown in FIG. 1.

FIG. 2 is a block diagram illustrating an example computer for implementing the converter system 100 shown in FIG. 1. The computer 200 includes at least one processor 202 coupled to a chipset 204. The chipset 204 includes a memory controller hub 220 and an input/output (I/O) controller hub 222. A memory 206 and a graphics adapter 212 are coupled to the memory controller hub 220, and a display 218 is coupled to the graphics adapter 212. A storage device 208, input interfaces 214, and network adapter 216 are coupled to the I/O controller hub 222. Other embodiments of the computer 200 have different architectures.

The storage device 208 is a non-transitory computer-readable storage medium such as a hard drive, compact disk read-only memory (CD-ROM), DVD, or a solid-state memory device. The memory 206 holds instructions and data used by the processor 202. The input interfaces 214 may include a touch-screen interface, a mouse, track ball, or other type of pointing device, a keyboard, a scanner or other conventional digitizer, or some combination thereof, and is used to input data, including images of radiology film 101, into the computer 200. The graphics adapter 212 displays images and other information on the display 218. The network adapter 216 couples the computer 200 to one or more computer networks.

The computer 200 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 208, loaded into the memory 206, and executed by the processor 202.

The type of computer 200 used for converter system 100 can vary depending upon the embodiment. For example, the converter system 100 may include multiple computers 200 communicating with each other through a network to provide the functionality described herein. Such computers 200 may lack some of the components described above, such as graphics adapters 212 and displays 218.

Grid Block Segmentation

Figure 3:
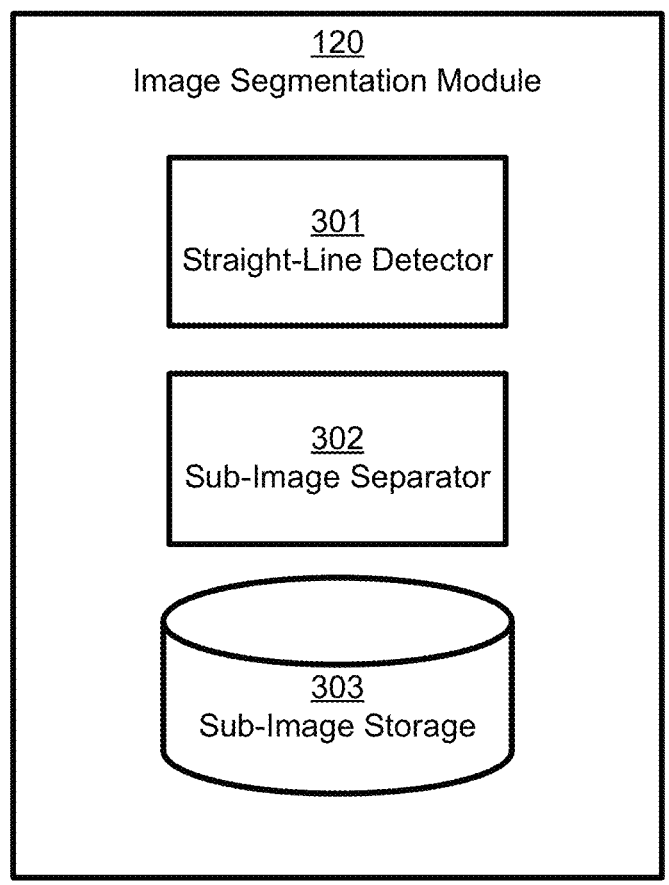
FIG. 3 is a block diagram illustrating an image segmentation module of a converter system in accordance with an embodiment.

FIG. 3 is a block diagram illustrating an image segmentation module 120 of a converter system 100 in accordance with an embodiment. The image segmentation module 120 identifies a grid pattern in the scanned image in order to accurately segment it into grid block sub-images. In this example, the image segmentation module 120 includes a straight-line detector 301, a sub-image separator 302, and sub-image storage 303.

The straight-line detector 301 of the image segmentation module 120 of the converter system 100 detects straight lines within the image. In one embodiment, the straight-line detector 301 applies an edge-detection pre-processing step according to any edge-detection methodology known to those of skill in the art. An edge-detection pre-processing step may be used to identify or strengthen edges in the image by improving contrast between foreground and background before subsequent processing by the straight-line detector 301. The straight-line detector 301 applies a Hough Transform to the pre-processed image data to detect straight lines in the image. The straight-line detector 301 uses a statistical analysis on the results of the Hough Transform that separately considers the length of the detected lines at vertical and horizontal positions in order to remove false-positive gridlines from the group of detected straight lines. The straight-line detector 301 clusters the remaining straight lines together if they are within a short distance of each other. The straight-line detector 301 identifies the mean position of each cluster of lines in the vertical direction as the center of a vertical gridline, and the mean position of each cluster of lines in the horizontal direction as the center of a horizontal gridline. These operations will be described in more detail with reference to the flowcharts of FIGS. 4-5.

Referring again to FIG. 3, the sub-image separator 302 of the image segmentation module 120 uses the detected positions of the horizontal and vertical gridlines from the straight-line detector 301 to divide the image accurately into sub-images. For example, each sub-image may include an image from a single x-ray from among the patient's plurality of x-rays collected on the radiology film 101.

The sub-image storage 303 at least temporarily stores the sub-images processed by the image segmentation module 120 for further processing by the converter system 100. Because such sub-images may include sensitive patient health information, adequate safeguards may be included in various implementations of the converter system 100 to prevent unauthorized access to the information and preserve patient confidentiality.

Figure 4:
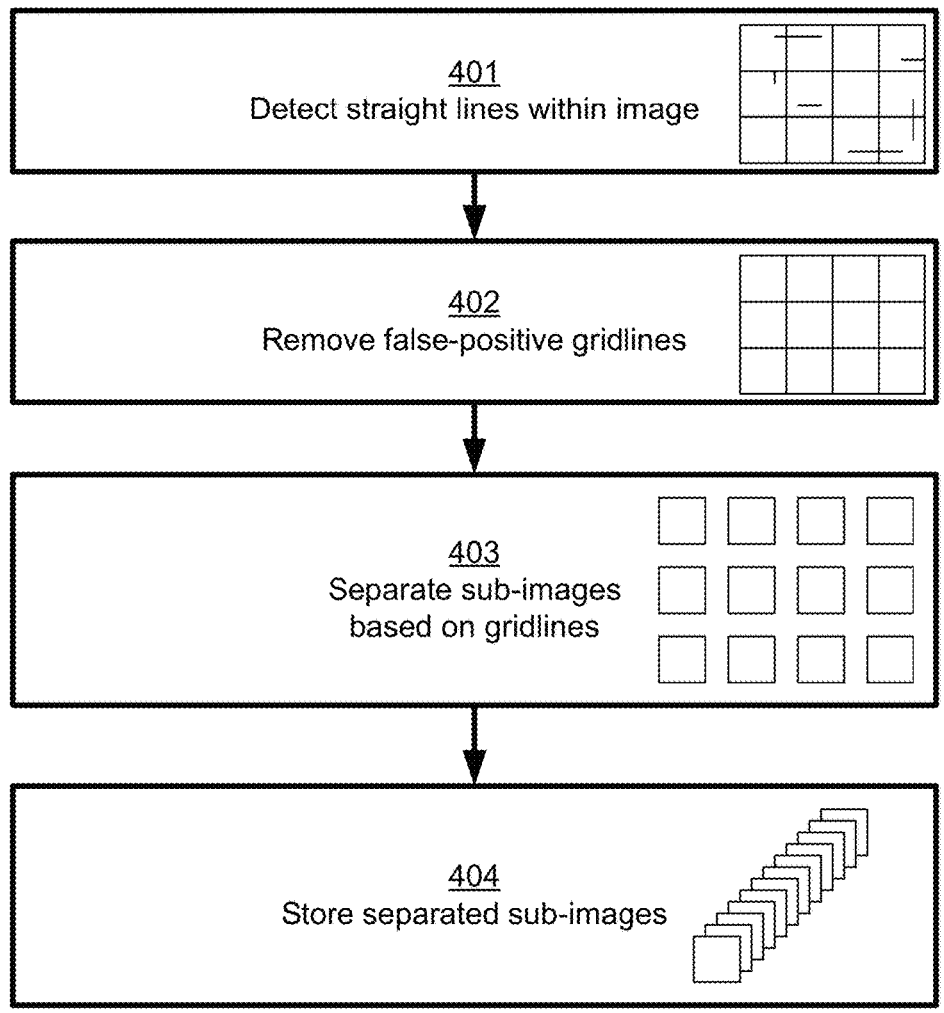
FIG. 4 is a flowchart illustrating a method of performing grid block segmentation on an image of a radiology film in accordance with an embodiment.

FIG. 4 illustrates a method of performing grid block segmentation on an image of a radiology film in accordance with an embodiment. The method is described as being performed by the image segmentation module 120 of the converter system 100, but other modules may perform steps of the method. Further, in various implementations, different or additional steps may be performed to segment an image of radiology film 101 into sub-images.

In step 401, straight lines within the image of the radiology film 101 are detected. Some of these straight lines are gridlines that divide an image into sub-images. Others of these lines are false-positive gridlines that may occur as the result of anatomical features, text content, or other features in the image that appear to be straight-lines when processed by the image segmentation module 120. In step 402, false-positive gridlines are removed from consideration as gridlines between sub-images. Techniques for detecting 401 straight lines within images and removing 402 false-positive gridlines are discussed in more detail below with reference to FIGS. 5-6. In step 403, the sub-images are separated based on the gridlines, and in step 404, the separated sub-images are stored, for example in sub-image storage 303 for further processing by the converter system 100.

Figure 5:
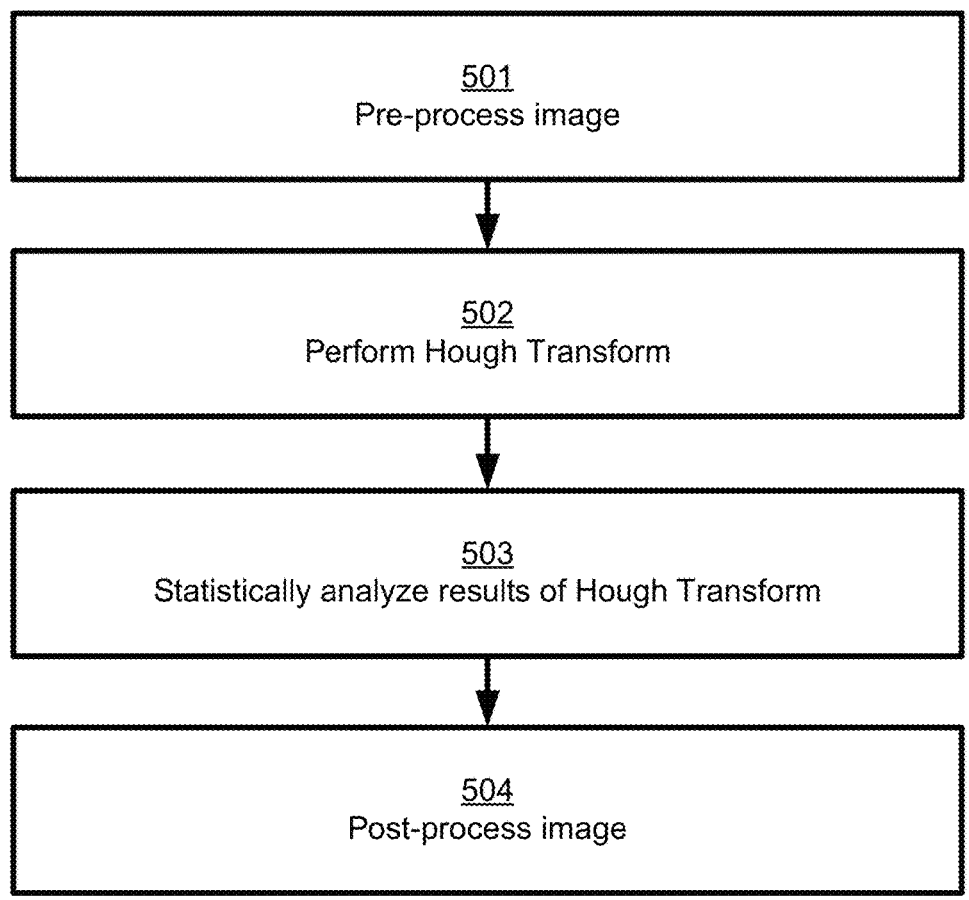
FIG. 5 is a flowchart illustrating a method of processing an image to detect straight lines and remove false-positive gridlines in accordance with an embodiment.

FIG. 5 is a flowchart illustrating a method of processing an image to detect straight lines and remove false-positive gridlines in accordance with an embodiment. The method is described as being performed by the image segmentation module 120 of the converter system 100, but other modules may perform steps of the method. Further, in various implementations, different or additional steps may be performed to detect straight lines and remove false-positive gridlines.

In some implementations, in step 501, the image is pre-processed using an edge-detection technique. Any edge-detection technique known to those of skill in the art may be used, such as Canny or Sobel operator, in order to identify or strengthen edges in the image.

In step 502, a Hough Transform is applied. The Hough Transform identifies lines by a voting procedure carried out in parameter space. However, the Hough Transform has several drawbacks when applied to radiology films. First, the images tend to have large intensity variations which lead to the Hough Transform reporting many false positive lines. In addition, the presence of text in the image creates strong edges that lead to confident Hough lines. If not remedied, the false positive lines stemming from intensity variations and text within an image would lead to over-segmentation of the image into odd-shaped portions of images rather than discrete sub-images divided by gridlines. Second, the voting parameters of the Hough Transform are image dependent, which leads to variations in the output. Third, the Hough Transform is subject to false negatives which would lead to under-segmentation of the radiology film.

In step 503, the results of the Hough Transform are statistically analyzed to reduce the false positives and false negatives discussed above. A detailed example of the statistical analysis is described below with reference to FIG. 6.

In step 504, the image may be post-processed to prepare it for separation into sub-images. Various conventional image post-processing techniques may be used. In post-processing, the results obtained from statistical analysis can be further refined. For example, the distance between each line in the set of distinct gridlines obtained by statistical analysis is calculated and the common repeating distance is voted as the gridblock/sub-image size. This added information can then be used to cut the grid into sub-images which will now have the same aspect ratio.

Figure 6:
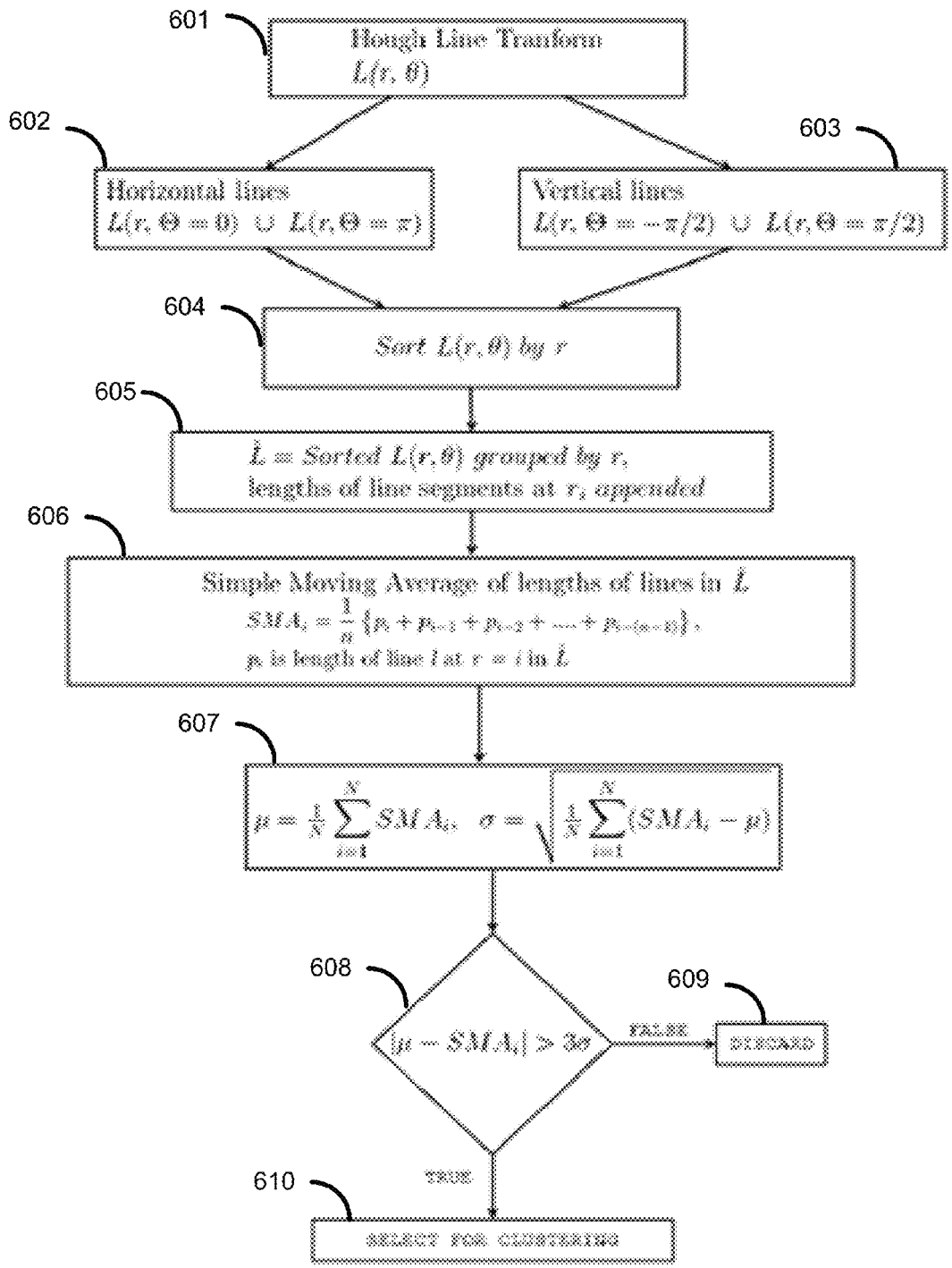
FIG. 6 is a flowchart illustrating a method of identifying a grid pattern in an image of a radiology film.

FIG. 6 is a flowchart illustrating an example method of identifying a grid pattern in an image of a radiology film by using a Hough Transform and statistically analyzing the results, in accordance with an embodiment of the invention. In some implementations, variations of the illustrated steps may be performed, some steps may be omitted, or the steps may be performed in different orders.

In step 601, a Hough Line Transform is performed. As described above, the Hough Transform tends to result in false positives and false negatives. To reduce the instances of these false positives and false negatives, the method continues by finding the horizontal lines in step 602 and the vertical lines in step 603, and then to sort the horizontal and vertical lines separately by distance from an origin, r, in step 604. Next, the sorted lines are grouped by r and the lengths of the line segments at each distance $r_i$ are appended. This prepares the detected line segments for finding a Simple Moving Average of lengths of the lines in step 606. In step 607, the mean and standard deviation are determined for the distribution of the Simple Moving Average, which in one embodiment is a normal distribution. In step 608, if the Simple Moving Average at a particular point is less than or equal to three standard deviations away from the mean, then the line is discarded as a false positive in step 609. In step 610, if the Simple Moving Average at a particular point is more than three standard deviations away from the mean, then the line is selected for clustering in step 610. In other embodiments, different cutoffs, such as 2.5 standard deviations may be used to adjust the number of false positives that are discarded 609 versus lines selected for clustering 610. The straight-line detector 301 clusters the remaining straight lines together if they are within a short distance of each other, for example if they are within approximately 1% of the image dimension. For example, for a 4000 pixel image dimension, the segments within 40 pixels will be clustered together. The straight-line detector 301 identifies the mean position of each cluster of lines in the vertical direction as the center of a vertical gridline, and the mean position of each cluster of lines in the horizontal direction as the center of a horizontal gridline. To identify missing lines between grid blocks, the grid block size is estimated using a voting procedure. The distance is calculated between each line in the set of distinct gridlines obtained by statistical analysis, and the common repeating distance is voted as the distance between the gridlines that makes up a single grid block. This repeating distance is used to extrapolate and add the missing lines between grid blocks.

Figure 7A:
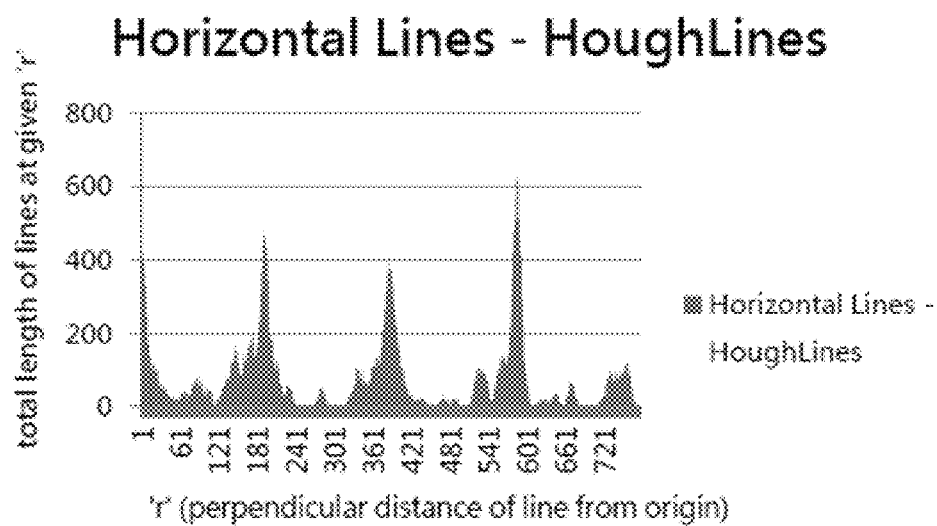
FIG. 7A illustrates an example graph of the length of horizontal HoughLines at various distances from the origin.
Figure 7B:
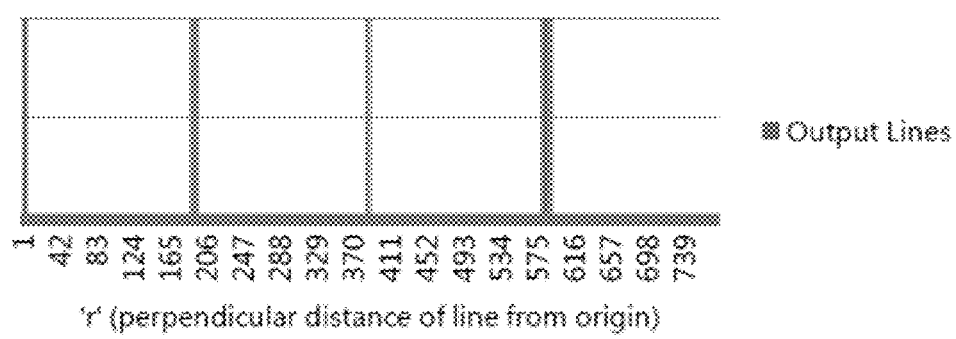
FIG. 7B illustrates an example output of lines from the statistical analysis of the data in FIG. 7A according to the method illustrated in FIG. 6.

FIG. 7A illustrates an example graph of the length of horizontal HoughLines at various distances from the origin. FIG. 7B illustrates an example output of lines from the statistical analysis of the data in FIG. 7A according to the method illustrated in FIG. 6. As can be seen in FIG. 7B, strong lines in tight clusters are returned at relatively evenly spaced distances from the origin, which correspond to horizontal gridlines between the sub-images.

Figure 8A:
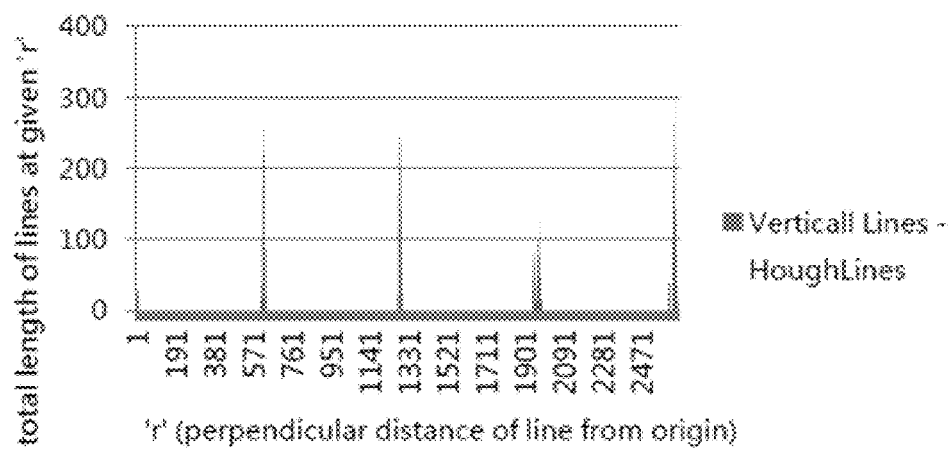
FIG. 8A illustrates an example graph of the length of vertical HoughLines at various distances from the origin.
Figure 8B:
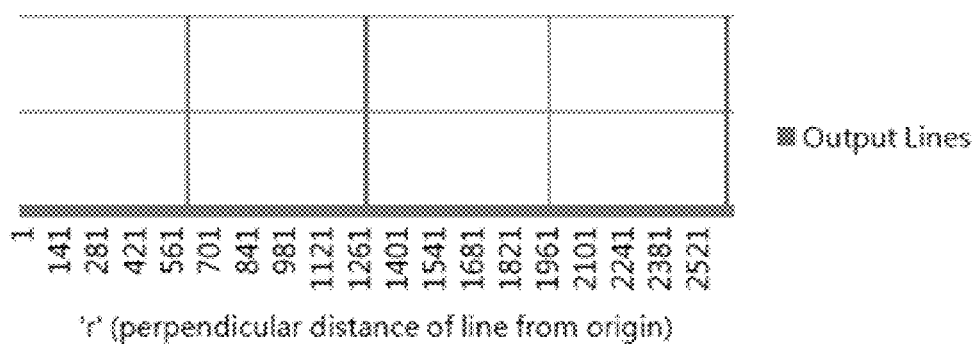
FIG. 8B illustrates an example output of lines from the statistical analysis of the data in FIG. 8A according to the method illustrated in FIG. 6.

FIG. 8A illustrates an example graph of the length of vertical HoughLines at various distances from the origin. FIG. 8B illustrates an example output of lines from the statistical analysis of the data in FIG. 8A according to the method illustrated in FIG. 6. As can be seen in FIG. 8B, strong lines in tight clusters are returned at four relatively evenly spaced distances from the origin, which correspond to vertical gridlines between the sub-images.

The positions of the gridlines shown in FIGS. 7B and 8B are used by the sub-image separator 302 of the image segmentation module 120 to divide the image accurately into sub-images. Thus, embodiments of the invention avoid over-segmentation and under-segmentation of the image that are common problems with the bare application of the Hough Transform by using a statistical analysis of the Hough transform results to identify gridlines between sub-images.

Text Processing

Figure 9:
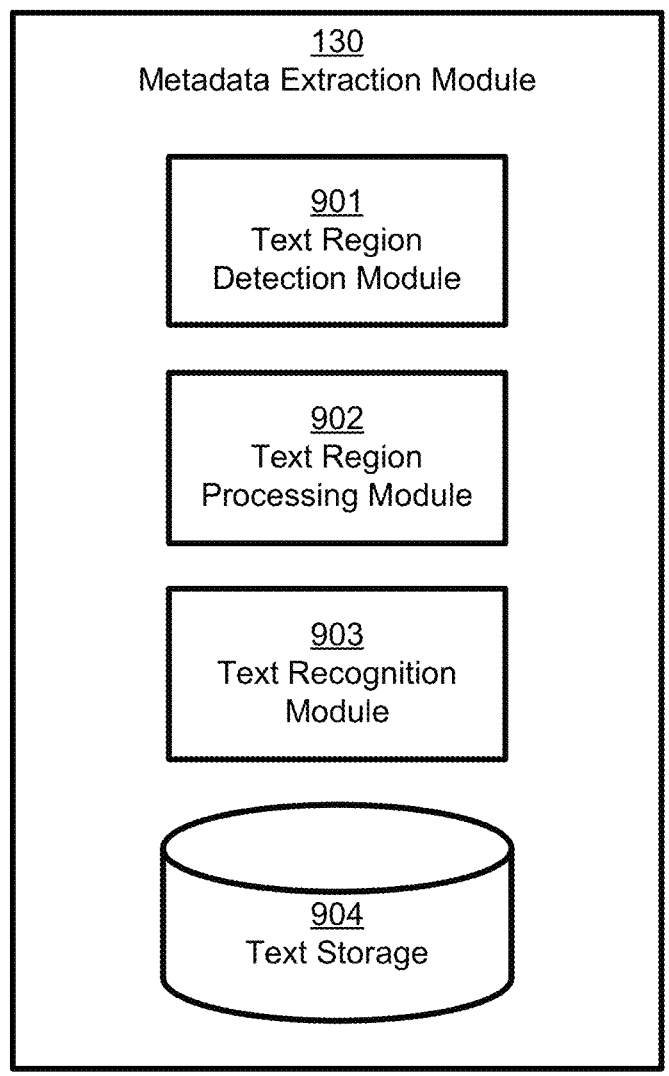
FIG. 9 is a block diagram illustrating a metadata extraction module of a converter system in accordance with an embodiment.

FIG. 9 is a block diagram illustrating a metadata extraction module of a converter system in accordance with an embodiment. The metadata extraction module extracts text from the scanned radiology film 101 to be used as DICOM metadata for a DICOM-compliant file. The metadata extraction module 130 includes a text region detection module 901, a text region processing module 902, a text recognition module 903, and text storage 904.

The text region detection module 901 detects regions of the image that contain text. An example of a method that the text region detection module 901 may apply to detect text regions is described below with reference to FIG. 10.

The text region processing module 902 processes the text regions to prepare them for successful text recognition. An example of a method that the text region processing module 902 may apply to process text regions is described below with reference to FIG. 11.

The text recognition module 903 performs optical character recognition. An example of a method that the text recognition module 903 may apply to recognize text is described below with reference to FIG. 13.

The text storage 904 stores the text recognized by the text recognition module 903. The stored text is used as DICOM metadata for the DICOM-compliant file that includes the associated sub-image from which the text was extracted.

Figure 10:
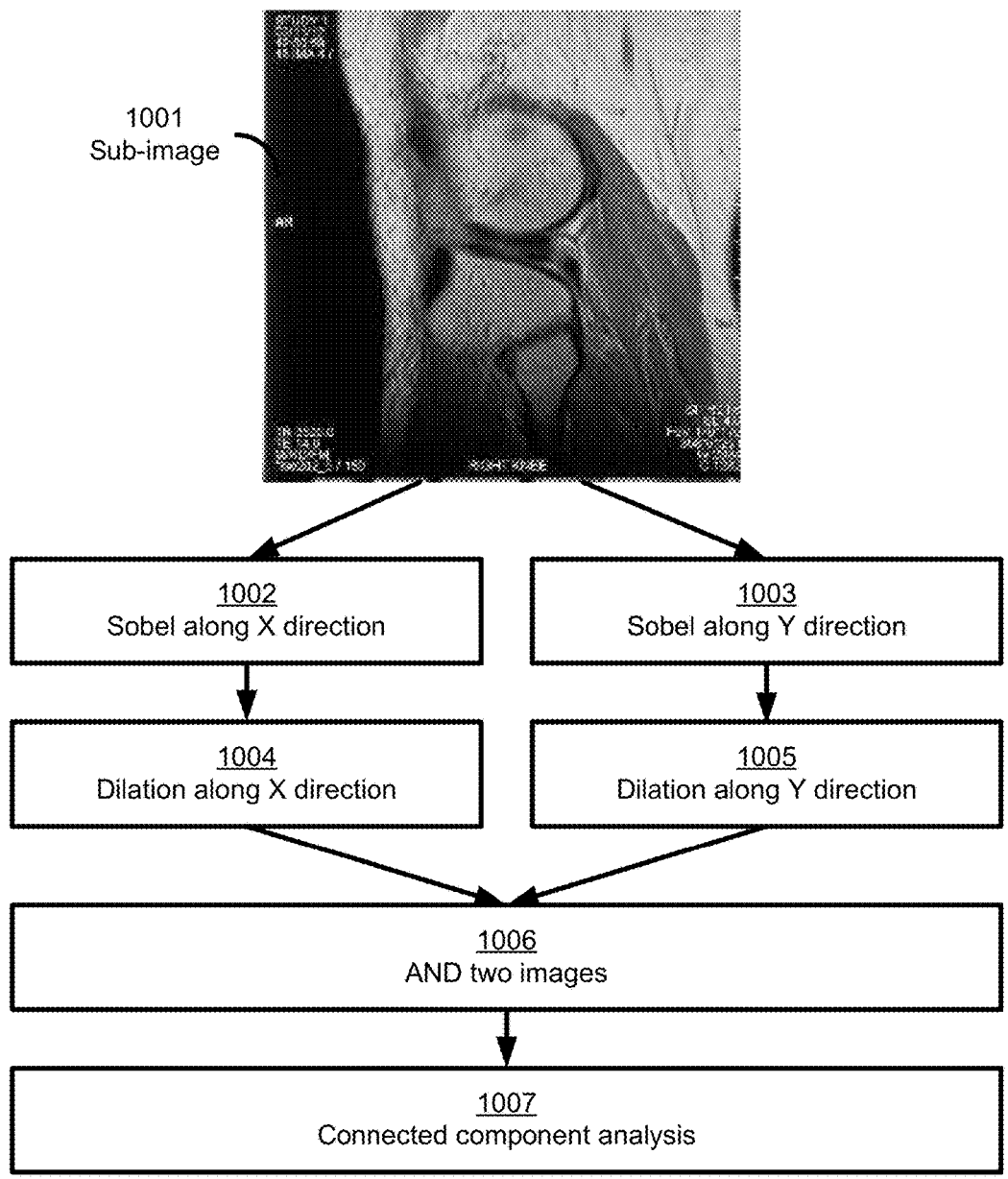
FIG. 10 is a flowchart illustrating a method of text region detection in accordance with an embodiment.

FIG. 10 is a flowchart illustrating a method of text region detection in accordance with an embodiment. This method may be performed, for example, by a text region detection module 901 of a metadata extraction module 130 of the converter system 100. In some implementations, variations of the illustrated steps may be performed, some steps may be omitted, or the steps may be performed in different orders. The method presented here is similar to the method proposed by Chen, Bourlard, and Thiran in "Text Identification in Complex Backgrounds Using SVM," Proceedings of the 2001 IEEE Computer Society Conference on Computer Vision and Pattern Recognition. Text regions can be detected in part by looking for short edge mixture patterns within a region. The method begins with a sub-image 1001 to be analyzed. In steps 1002 and 1003, the horizontal and vertical edges present in text regions are found by using a Sobel operator along the X direction and using a Sobel operator along the Y direction. Then, in steps 1004 and 1005, morphological dilation along the X direction and along the Y direction are performed to connect edges into clusters. In one embodiment, different dilation operators can be used so that vertical edges are connected in the horizontal direction and horizontal edges are connected in the vertical direction. The dilation operations may have a rectangular shape, such as 5×1 for the vertical operator and 3×6 for the horizontal operator. In step 1006, the resulting two images are combined using a binary AND operation because true text regions will have horizontal and vertical edges within the same region of the image. Additionally, in step 1007, a conventional connected component analysis is performed to identify the boundaries of the regions of the sub-image where text is present.

Figure 11:
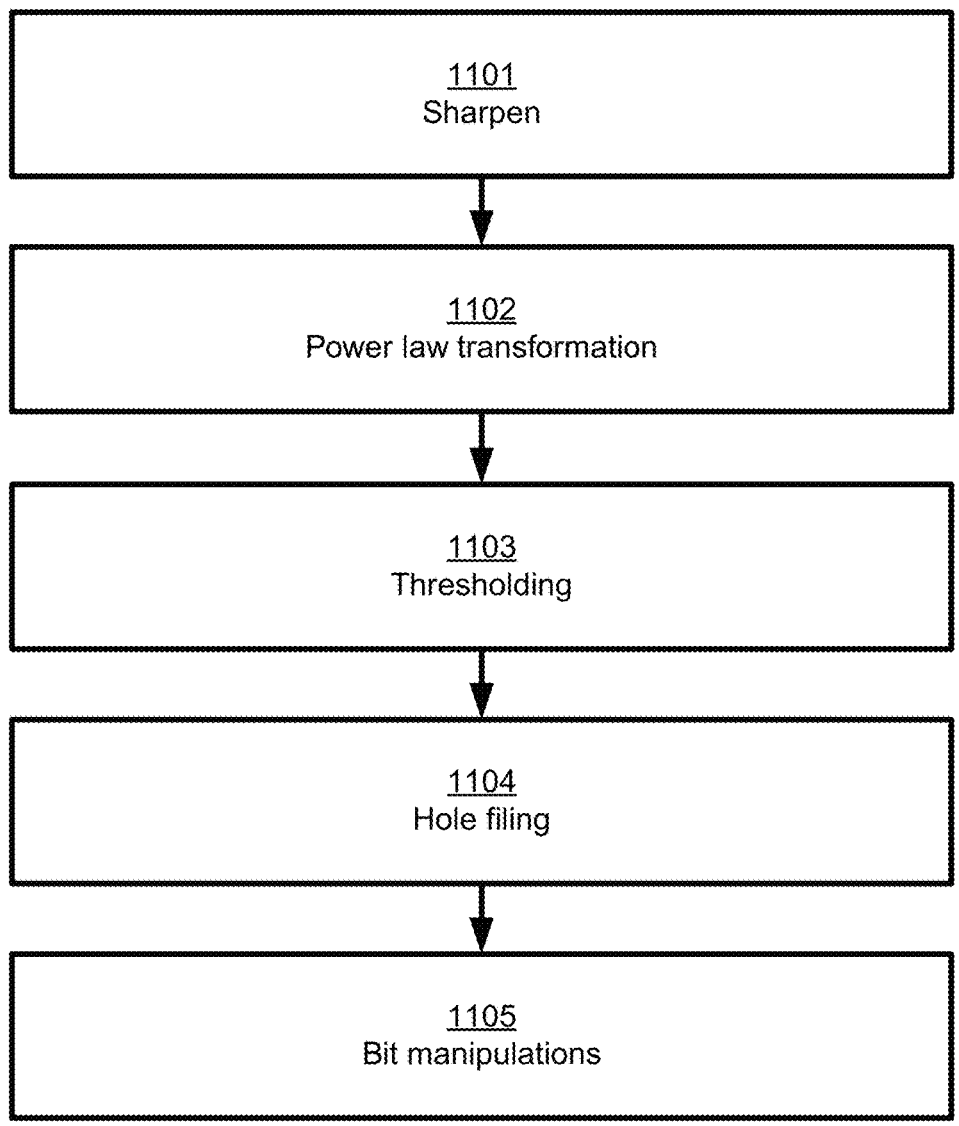
FIG. 11 is a flowchart illustrating a method of processing text regions to prepare them for text recognition in accordance with an embodiment.
Figure 12:
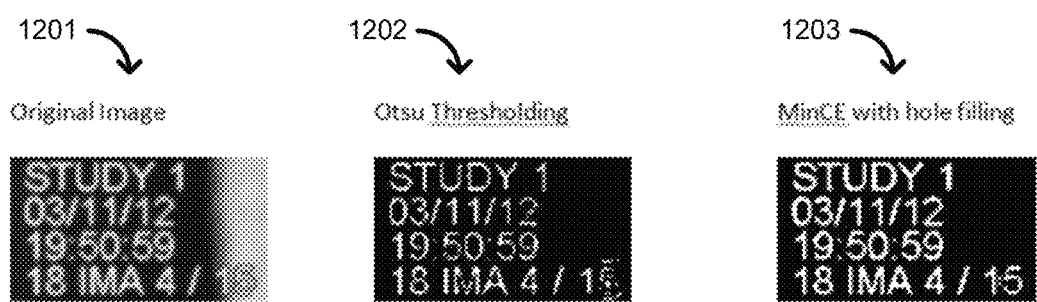
FIG. 12 illustrates a comparison between text regions from the original image, text regions processed according to a conventional Otsu Thresholding technique, and text regions processed according to techniques in accordance with an embodiment of the invention, referred to as MinCE with hole filing.

FIG. 11 is a flowchart illustrating a method of processing text regions to prepare them for text recognition in accordance with an embodiment. This method may be performed, for example, by a text region processing module 902 of a metadata extraction module 130 of the converter system 100. In some implementations, variations of the illustrated steps may be performed, some steps may be omitted, or the steps may be performed in different orders. The method begins with sharpening 1101 the identified text regions according to any standard technique known to those of skill in the art. Then, a power law transformation 1102, for example $\gamma=4$, is applied to the image data of the sharpened text regions. Next, a thresholding 1103 process is applied, for example using Minimum Cross Entropy (MinCE), as described by Li and Lee in "Minimum Cross Entropy Thresholding," Pattern Recognition, Vol. 26, No. 4, pp. 617-625, 1993. MinCE is a standard technique known to those of skill in the art that minimizes the cross entropy between the threshold image and the original image. The selection of a threshold will affect both the accuracy and the efficiency of the analysis of the segmented image. The best threshold loses the least information during the thresholding. Advantageously, no a priori assumptions are made about the population distribution during the MinCE thresholding process. After the thresholding 1103, hole filling 1104 is performed. Hole filing is a mathematical operation that fills all gaps in the identified text region according to standard techniques known to those of skill in the art. Lastly, in some implementations, bit manipulations 1105 are performed, for example an XOR operation is performed between one version of the image of the text region that is thresholded, and another version of the image of the text region that is thresholded and hole-filled. FIG. 12 illustrates a comparison between text regions from the original image 1201, text regions processed according to a conventional Otsu Thresholding technique 1202, and text regions processed according to techniques in accordance with an embodiment of the invention, referred to as MinCE with hole filling 1203. The text regions processed according to MinCE with hole filling are substantially improved, with less interference from the complex background than the original image text regions 1201 or the Otsu Thresholding text regions 1202.

Figure 13:
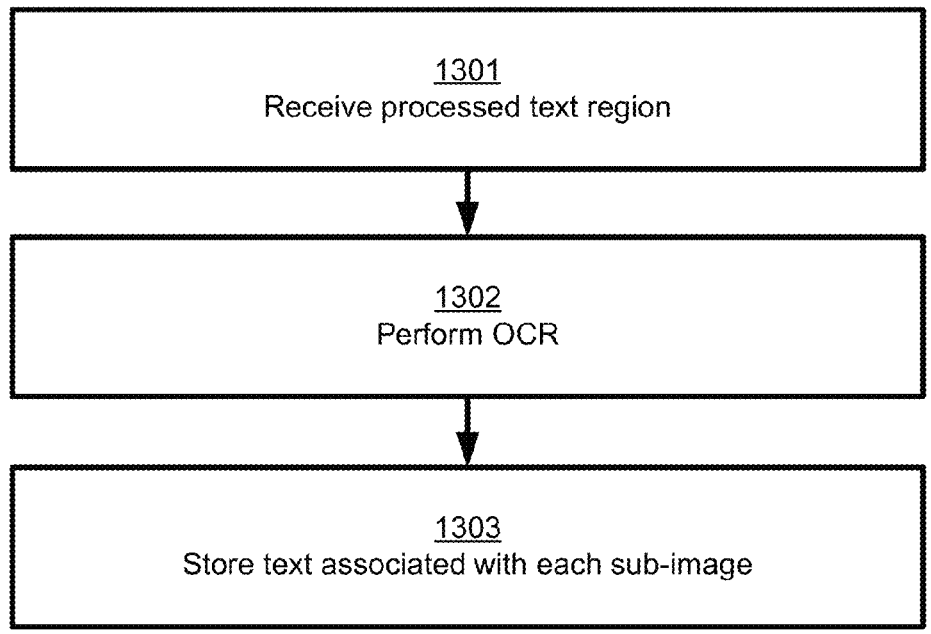
FIG. 13 is a flowchart illustrating a method of performing text recognition in accordance with an embodiment.

FIG. 13 is a flowchart illustrating a method of performing text recognition in accordance with an embodiment. This method may be performed, for example, by a text recognition module 903 of a metadata extraction module 130 of the converter system 100. The method begins in step 1301 by receiving a processed text region, for example from text region processing module 902 of the metadata extraction module 130. In step 1302, optical character recognition is performed on the processed text region in order to recognize the text contained in the region. Any technique of optical character recognition known to those of skill in the art may be used. In step 1303, the recognized text associated with a respective sub-image from which it was extracted is stored. Thus, the recognized text is available for use as DICOM metadata in a DICOM-compliant file including the analyzed sub-image.

In one embodiment, an evaluation tool can be used to evaluate the text extraction by using the Levenshtein Distance between the ground truth (the actual text) and the text recognized by the OCR process 1302. For example, the analysis can be performed using 1-e/c, where e is the Levenshtein distance, and c is the number of characters. Such an evaluation tool applied to the text extraction resulting from the methods described above shows that the methods described above perform substantially better than OCR processes on text regions that have not been processed according to the methods described above.

DICOM File Generation

Figure 14:
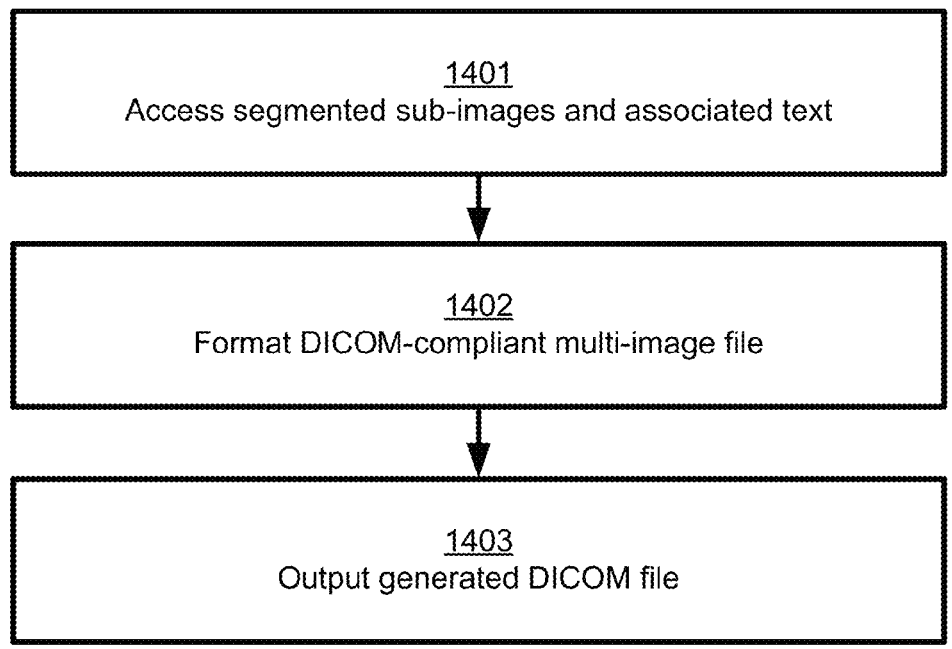
FIG. 14 is a flowchart illustrating a method of generating a DICOM file in accordance with an embodiment.

FIG. 14 is a flowchart illustrating a method of generating a DICOM file in accordance with an embodiment. This method may be performed, for example, by a DICOM file generation module 140 of the converter system 100. In some implementation, variations of the illustrated steps may be performed. In step 1401, the segmented sub-images and associated text are accessed, for example from sub-image storage 303 of the image segmentation module 120 and from text storage 904 of the metadata extraction module 130. In step 1402, a DICOM-compliant multi-image file is formatted according to the DICOM standard, including the associated text as DICOM metadata. In step 1403, the generated DICOM file can be output, for example to a different computer system for analysis, treatment, or research purposes.

Advantageously, the described converter system 100 can be integrated on top of the image acquisition software of medical scanners. Thus, the images from the medical scanners conveniently can be converted through the converter system 100 into a DICOM-compliant file 141 without delay. Alternatively, the described converter system 100 can be used as a research tool to remove all patient related information by redacting recognized text that contains confidential patent information from the DICOM file before it is shared with researchers. Thus, the images can then be used for research purposes appropriate to the type of image (e.g., classification of tissue, detection of tumor/fracture, etc.), without the risk of exposing sensitive information in violation of privacy laws.

Additional Configuration Considerations

Some portions of the above description describe the embodiments in terms of algorithmic processes or operations. These algorithmic descriptions and representations are commonly used by those skilled in the data processing arts to convey the substance of their work effectively to others skilled in the art. These operations, while described functionally, computationally, or logically, are understood to be implemented by computer programs comprising instructions for execution by a processor or equivalent electrical circuits, microcode, or the like. Furthermore, it has also proven convenient at times, to refer to these arrangements of functional operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the disclosure. This description should be read to include one or at least one and the singular also includes the plural unless it is obvious that it is meant otherwise.

Upon reading this disclosure, those of skill in the art will appreciate still additional alternative structural and functional designs. Thus, while particular embodiments and applications have been illustrated and described, it is to be understood that the described subject matter is not limited to the precise construction and components disclosed herein and that various modifications, changes and variations which will be apparent to those skilled in the art may be made in the arrangement, operation and details of the method and apparatus disclosed herein.

What is claimed is:

1. A computer-implemented method comprising:
performing a Hough Transform to detect straight lines within an image of a scanned radiology film, the image including a plurality of sub-images in a grid pattern;
discarding false positives from the detected straight lines based on a statistical analysis of lengths of the detected straight lines;
identifying gridlines between sub-images based on a clustering of remaining detected straight lines;
separating sub-images based on the gridlines; and
storing the separated sub-images.

2. The method of claim 1, wherein discarding the false positives from the detected straight lines comprises:
finding a Simple Moving Average of the lengths of the detected straight lines sorted by distance from an origin;
determining a mean and standard deviation of a distribution of the Simple Moving Average; and
discarding a line as a false positive responsive to the Simple Moving Average corresponding to the line being less than a cutoff number of standard deviations from the mean.

3. The method of claim 1, further comprising detecting text regions within the sub-images by:
detecting horizontal and vertical edges of the text regions by applying Sobel operators along an X direction and along a Y direction;
connecting the detected horizontal and vertical edges into clusters by performing morphological dilation along the X direction and along the Y direction; and
performing a binary AND operation to identify text regions that have horizontal and vertical edges within a same region of a respective sub-image.

4. The method of claim 1, further comprising:
detecting text regions within the sub-images;
applying Minimum Cross Entropy thresholding to detected text regions; and
performing hole filling on the detected text regions.

5. The method of claim 1, further comprising:
detecting text regions within the sub-images;
performing optical character recognition to recognize text from a respective text region of a respective sub-image; and
storing the text associated with the respective sub-image.

6. The method of claim 5, further comprising:
accessing the separated sub-images and text associated with the respect sub-images;
formatting a DICOM-compliant multi-image file based on the sub-images and associated text; and
outputting the DICOM-compliant file.

7. A non-transitory computer-readable storage medium storing executable computer program instructions, the instructions executable to perform steps comprising:
performing a Hough Transform to detect straight lines within an image of a scanned radiology film, the image including a plurality of sub-images in a grid pattern;
discarding false positives from the detected straight lines based on a statistical analysis of lengths of the detected straight lines;
identifying gridlines between sub-images based on a clustering of remaining detected straight lines;
separating sub-images based on the gridlines; and
storing the separated sub-images.

8. The medium of claim 7, wherein discarding the false positives from the detected straight lines comprises:
finding a Simple Moving Average of the lengths of the detected straight lines sorted by distance from an origin;
determining a mean and standard deviation of a distribution of the Simple Moving Average; and
discarding a line as a false positive responsive to the Simple Moving Average corresponding to the line being less than a cutoff number of standard deviations from the mean.

9. The medium of claim 7, further comprising detecting text regions within the sub-images by:
detecting horizontal and vertical edges of the text regions by applying Sobel operators along an X direction and along a Y direction;
connecting the detected horizontal and vertical edges into clusters by performing morphological dilation along the X direction and along the Y direction; and
performing a binary AND operation to identify text regions that have horizontal and vertical edges within a same region of a respective sub-image.

10. The medium of claim 7, the steps further comprising:
detecting text regions within the sub-images;
applying Minimum Cross Entropy thresholding to detected text regions; and
performing hole filling on the detected text regions.

11. The medium of claim 7, the steps further comprising:
detecting text regions within the sub-images;
performing optical character recognition to recognize text from a respective text region of a respective sub-image; and
storing the text associated with the respective sub-image.

12. The medium of claim 11, the steps further comprising:
accessing the separated sub-images and text associated with the respect sub-images;
formatting a DICOM-compliant multi-image file based on the sub-images and associated text; and
outputting the DICOM-compliant file.

13. A system comprising:
a processor configured to execute modules; and
a memory storing the modules, the modules comprising:
an image segmentation module comprising:
a straight-line detector configured to
perform a Hough Transform to detect straight lines within an image of a scanned radiology film, the image including a plurality of sub-images in a grid pattern,
discard false positives from the detected straight lines based on a statistical analysis of lengths of the detected straight lines, and
identify gridlines between sub-images based on a clustering of remaining detected straight lines;
a sub-image separator configured to separate sub-images based on the gridlines; and
a sub-image storage configured to store the separated sub-images.

14. The system of claim 13, wherein the modules further comprise a metadata extraction module comprising a text region detection module configured to detect text regions within the sub-images.

15. The system of claim 14, wherein the metadata extraction module further comprises:
a text region processing module; and
a text recognition module configured to recognize text from text regions of respective sub-images.

16. The system of claim 15, wherein the modules further comprise a DICOM file generation module configured to format a DICOM-compliant multi-image file based on the sub-images and the recognized text.

17. The method of claim 1, wherein identifying the gridlines between sub-images based on the clustering of the remaining detected straight lines comprises:
   clustering remaining detected straight lines within a short distance of each other; and
   identifying a mean position of each cluster as a position of a gridline.

18. The method of claim 1, wherein identifying gridlines between sub-images based on the clustering of the remaining detected straight lines comprises:
   determining a common repeating distance between gridlines identified by the clustering; and
   identifying missing gridlines by extrapolating according to the common repeating distance from the gridlines identified by the clustering.

19. The medium of claim 7, wherein identifying the gridlines between sub-images based on the clustering of the remaining detected straight lines comprises:
   clustering remaining detected straight lines within a short distance of each other; and
   identifying a mean position of each cluster as a position of a gridline.

20. The medium of claim 7, wherein identifying gridlines between sub-images based on the clustering of the remaining detected straight lines comprises:
   determining a common repeating distance between gridlines identified by the clustering; and
   identifying missing gridlines by extrapolating according to the common repeating distance from the gridlines identified by the clustering.

* * * * *